United States Patent [19]

Reid

[11] 4,200,107
[45] Apr. 29, 1980

[54] VASCULAR CONNECTOR FOR EFFECTING VASCULAR DUCT CLOSURE AND PERMITTING VASCULAR RE-OPENING

[76] Inventor: Robert L. Reid, 7450 E. Bonita Dr., Scottsdale, Ariz. 85253

[21] Appl. No.: 851,858

[22] Filed: Nov. 16, 1977

[51] Int. Cl.² .................... A61B 17/00; A61B 17/12
[52] U.S. Cl. .......................... 128/305; 128/334 C; 128/335; 128/346; 137/318; 138/97; 285/DIG. 22
[58] Field of Search ............ 128/335, 305, 346, 334 R, 128/334 C, 1; 137/315, 318; 138/97, 98, 99; 30/131, 134; 29/213 R; 285/DIG. 22

[56] References Cited

U.S. PATENT DOCUMENTS

| | | | |
|---|---|---|---|
| 3,456,965 | 7/1969 | Gajewski et al. | 128/334 C |
| 3,687,166 | 8/1972 | Herrin | 137/318 |
| 3,704,704 | 12/1972 | Gonzales | 128/1 R |
| 3,820,528 | 6/1974 | Rogers | 128/1 R |
| 3,863,667 | 2/1975 | Ward | 137/318 |
| 3,933,158 | 1/1976 | Haverstock | 128/335 |
| 3,938,528 | 2/1976 | Bucalo | 128/334 C |
| 3,951,132 | 4/1976 | Bucalo | 128/334 R |
| 4,112,944 | 9/1978 | Williams | 128/346 |

Primary Examiner—Edgar S. Burr
Assistant Examiner—James R. Feyrer
Attorney, Agent, or Firm—Harry M. Weiss

[57] ABSTRACT

This disclosure relates to a vascular connector device which has features that permit the connector device to close a vascular duct and to subsequently permit the vascular duct to be re-opened, if desired. The vascular connector of this disclosure features a tubular shaped vascular connector having a guillotine type plunger arrangement or assembly which can be actuated for first closing and then re-opening the vascular duct, if desired. Also disclosed are two separate clamp mechanisms in the form of special tongs with one used for initially actuating the guillotine type plunger arrangement to close off the vascular duct and the other clamp mechanism is used for achieving opening of the vascular duct by moving the guillotine type plunger arrangement into another position which causes the vascular duct to re-open by means of the restoration of an open conduit through the vascular duct because of the alignment of both previously separated portions of the vascular duct with an aperture in the guillotine type plunger mechanism.

12 Claims, 9 Drawing Figures

VASCULAR CONNECTOR FOR EFFECTING VASCULAR DUCT CLOSURE AND PERMITTING VASCULAR RE-OPENING

BACKGROUND OF THE INVENTION

1. Field of the Invention

This invention relates generally to vascular connectors, and, more particularly, to vascular connectors used to effect closing and re-opening of vascular ducts.

2. Description of the Prior Art

In the past, surgical cutting and tying or clamping techniques have been utilized as the primary solution for separating vascular ducts or vessels which carry fluid when it was desired to prevent the passage of fluid through the vascular duct or vessel.

For example, one very common surgical technique for insuring that male sperm would not be transmitted from a male into a female was to cut and effectively separate the vascular vessel or duct that carried the male sperm known as a Vas Deferens. This surgical technique or procedure became known as a Vasectomy.

One major problem with this prior art surgical technique was that the procedure was not reversible which meant that one seeking to restore this vascular duct or vessel to its original function and operation could not achieve this because the surgical Vasectomy operation caused one cut end of the vascular duct or vessel to be effectively lost forever within the body of the male after being separated and after removal of a section from the other end of the vascular duct or vessel.

Thus, many males became extremely concerned about undergoing such an operation because of the psychological impact created by the knowledge that this surgical procedure was irreversible.

Accordingly, a need existed to provide a technique that could provide both the function of preventing male sperm from traveling through the vascular duct by the separation thereof as well as to permit the subsequent connection or opening of the vascular duct between the two separated portions in order to restore the function of having the male sperm be permitted to travel through the entire vascular duct.

SUMMARY OF THE INVENTION

It is an object of this invention to provide an improved vascular connector.

It is another object of this invention to provide an improved vascular connector that can function to prevent the passage of fluid through a vascular duct to which the vascular connector is connected.

It is still another object of this invention to provide an improved vascular connector that can function both to block the passage of fluid through the vascular duct to which the connector is connected, and to subsequently effect the opening of the vascular duct to permit fluid to pass through the vascular duct.

The foregoing and other objects, features and advantages of this invention will be apparent from the following more particular description of the preferred embodiments of the invention as illustrated in the accompanying drawings.

DESCRIPTION OF THE SPECIFICATIONS

Figure 1:
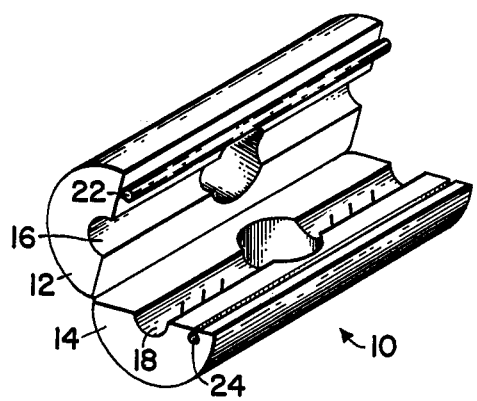
FIG. 1 is a perspective view showing the vascular connector in its opened position prior to being closed around a vascular duct or vessel.

Referring to FIG. 1, a vascular connector is generally designated by reference numeral 10. The vascular connector 10 is preferably formed in a cylindrical shape and is made of two parts which are pivotly connected together to move from its open position shown in FIG. 1 to its closed position as shown in the bottom portion of FIG. 2. The upper part or portion of the vascular connector 10 is designated by reference numeral 12 and the lower part or portion of the vascular connector 10 is designated by reference numeral 14. As can be seen with reference to FIG. 1, the upper part 12 of the vascular connector 10 has an elongated semi-circular shape and contains a longitudinally extending recess or groove 16. The semi-circular shape and longitudinally extending recess 16 of the upper part 12 of the vascular connector 10 matches up with the corresponding semi-circular shape and longitudinally extending recess 18 located in the bottom part 14 of the vascular connector 10 thereby providing a substantially cylindrical shaped opening 20 (see FIG. 2) through the axial center portion of the vascular connector 10 when the vascular connector 10 is in its closed position. A longitudinally extending male connector portion or member 22 is located in the upper part 12 of the vascular connector 10 and is used to engage a corresponding or mating longitudinally extending female type slot 24 located in the bottom part 14 of the vascular connector 10. Thus, as can be seen with reference to FIG. 2, the longitudinally extending male connector portion 22 press fits or snaps firmly into the longitudinally extending female slot 24 when the vascular connector 10 is in its closed position because of the outward curvature of the longitudinally extending male connector portion 22 and the receptive shape of the longitudinally extending female type slot 24 when the vascular connector 10 is in its closed position.

Figure 2:
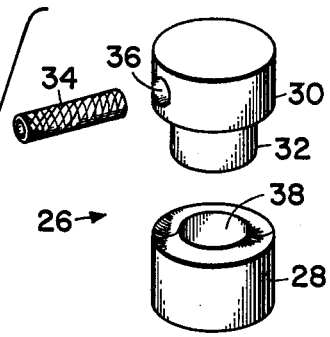
FIG. 2 is a view similar to FIG. 1, showing, however, the vascular connector in its closed position with its guillotine type plunger assembly shown in an exploded view above the transverse opening in the connector through which the assembly is inserted into the vascular connector in the position shown in FIG. 3A.
Figure 2:
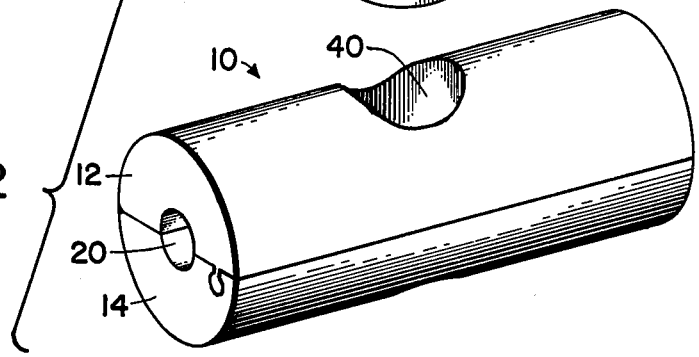

With specific reference to FIG. 2, a guillotine type assembly or mechanism is generally designated by reference numeral 26 which comprises a hollow cylindrical short tubular portion 28 and a piston type member 30 which has an extension member 32 connected to the piston type member 30. A hollow tubular shaped fibrous member 34 which is preferably of a material used in bypass surgery such as Dacron is used as an insert within opening 36 located in the piston type member 30. The reason for the use of this fibrous member 34 is explained below with respect to FIG. 4B.

The extension member 32 which is preferably integrally connected to the circumferentially larger piston member 30 fits within opening 38 located in the hollow cylindrical short tubular portion 28. The outer diameter of the hollow cylindrical short tubular portion 28 is the same diameter as the outerdiameter of the piston member 30 and both are slightly smaller than opening 40 which extends transversely through the vascular connector 10 (through the matching openings in the upper part 12 and the lower part 14 of the vascular connector 10). Thus, the piston member 30 and the short tubular portion 28 are slidably fitted within the opening 40 in the vascular connector 10 as described below.

Figure 3A:
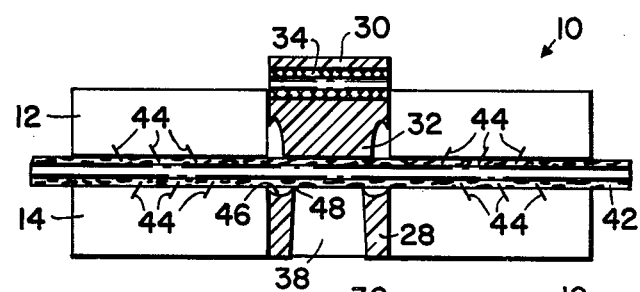
FIGS. 3A, 3B and 3C are cross-sectional views of the vascular connector showing the guillotine type plunger prior to being actuated to block a vascular duct portion located within the connector (FIG. 3A), in its intermediate position after actuation of the plunger assembly has begun (FIG. 3B), and in its vascular duct blocking position (FIG. 3C) which serves to cut and effectively block off the portion of the vascular duct or vessel which is located within the vascular connector.

Referring to FIG. 3A, this Figure is a cross-sectional view of the vascular connector 10 as it would appear in its closed position (as shown in FIG. 2) about a vascular duct or vessel 42 (only a part of which is shown). As can be seen with respect to FIG. 3A, the longitudinal or axial opening 20 (see FIG. 2) of the vascular connector 10 extends axially through the vascular connector 10 and has a diameter slightly larger than the vascular duct or vessel 42. Located within the axial opening 20 in the vascular connector 10 is a series of small prongs 44 (three each) which are shown on each side of the transverse opening 40 for both the upper part 12 and the lower part 14 of the vascular connector 10. These prongs 44 serve to provide a good gripping contact between the vascular connector 10 and the vascular duct or vessel 42 (due to the penetration into the wall of the vascular duct or vessel 42). This is important in the case of the use of the vascular connector for a Vasectomy type function because it provides a reliable connection.

As can be seen with reference to FIG. 3A, the guillotine type assembly or mechanism 26 is already in place in the vascular connector 10 in such a way that the short tubular portion 28 is located in the lower part 14 of the vascular connector 10 within the opening 40. The piston type member 30 and extension member 32 are located in the upper part 12 of the vascular connector 10 in such a manner or position that the upper portion of the piston type member 30 is raised slightly above the upper surface of the upper part 12 of the vascular connector 10 as is shown in FIG. 3A. This insertion of the guillotine type members or elements 30 (32) and 28 in the vascular connector 10 in the position shown in FIG. 3A is done prior to closing the vascular connector 10 around the vascular duct or vessel 42. In this initial position (FIG. 3A), the vascular connector 10 is closed about the vascular duct or vessel 42 and the vascular duct or vessel 42 is still functioning or operating to permit the passage of fluid thereto. The upper portion of the short tubular portion 28 has a circumferential recess 46 which thereby provides a circular shaped knife edge 48 that is located below a bottom surface portion of the piston type member 32. The importance of the knife edge 48 is more fully described below with respect to FIGS. 3B and 3C.

Figure 3B:
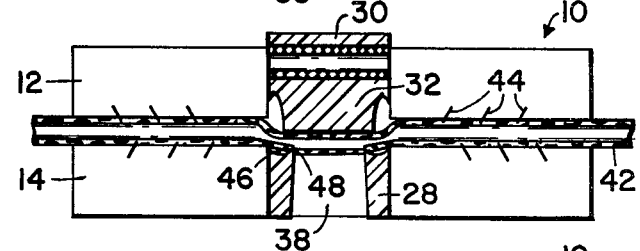
Figure 5:
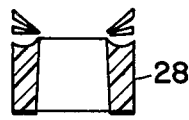
FIG. 5 is a perspective view of a surgical clamp mechanism which is used to close the vascular connector and operate the guillotine type plunger assembly to permit the cutting of the vascular duct or vessel as shown in FIGS. 3A, 3B and 3C.
Figure 5:
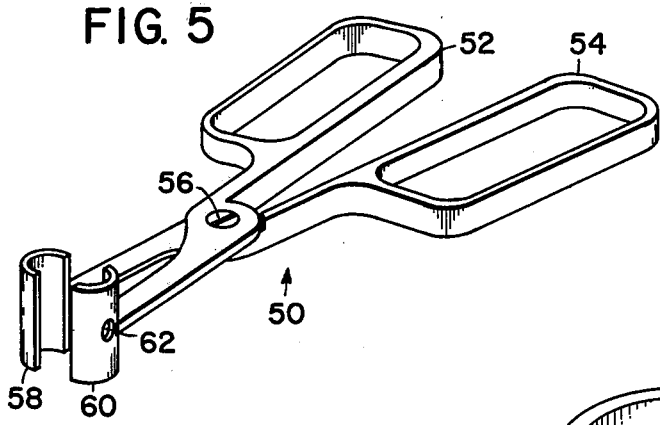

Referring to FIG. 3B, the piston type member 30 with its integrally connected extension member 32 is moved downwardly further into the transverse opening 40. This is done using the surgical clamp mechanism or assembly 50 (see FIG. 5). The surgical clamp assembly 50 (see FIG. 5) has a pair of arms 52 and 54 pivotly connected by pin 56 in order to permit opening and closing of clamp members 58 and 60 located at the ends of arms 54 and 52, respectively. Clamp member 58 is positioned above the upper part 12 of the vascular connector 10 and clamp member 60 is positioned below the bottom part 14 of the vascular connector 10 with opening 62 in the clamp member 60 disposed in alignment with the transverse opening 40 in the vascular connector 10. Thus, the clamp member 58 contacts the upper surface of the piston type member 30 and serves to move it downwardly as shown in FIG. 3B. This begins to bend the vascular duct 42 as shown in FIG. 3B beneath the bottom surface of the extension member 32.

Figure 3C:
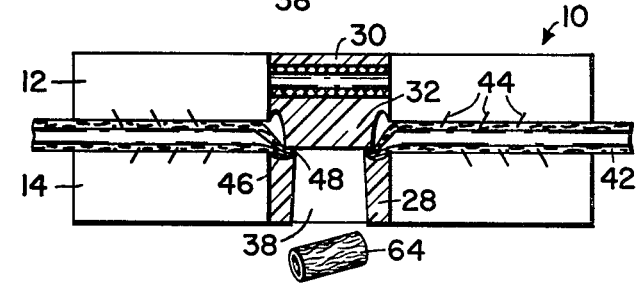

Referring to FIG. 3C, the clamp member 58 would now have reached its bottom-most position in contact with the clamp member 60 thus lowering the piston type member 30 completely into the transverse opening 40 of the vascular connector 10 thereby lining up the upper surface of the piston type member 30 with the upper surface of the upper part 12 of the vascular connector 10 (as shown by FIG. 3C). In this position the knife edge 48 on the short tubular portion 28 serves to cut off a piece 64 of the vascular duct (that is shown falling through opening 38 in the short tubular portion 28). The remaining two portions of the duct 42 are pinched off and held in place by the contact action of the extension member 32 with the short tubular portion 28 (and the prongs 44). FIGS. 3A, 3B and 3C show the sequence of steps to complete the operation of connecting the vascular connector 10 to the vascular duct or vessel 42 with the guillotine type apparatus or assembly 26 located within the vascular connector 10 being actuated by the clamp mechanism 50 to close off the vascular duct 42. Thus, the vascular connector 10 serves to maintain both separated parts of the vascular duct 42 in connection with each other by means of the vascular connector 10. Accordingly, as can be seen with reference to FIG. 3C, no fluid can pass from one end of the vascular duct 42 to the other end thereof because of the blockage created by the removal of the piece of the vascular duct 64 and the substitution there between of the extension member 32 which is in contact with the short tubular portion 28.

Figure 4A:
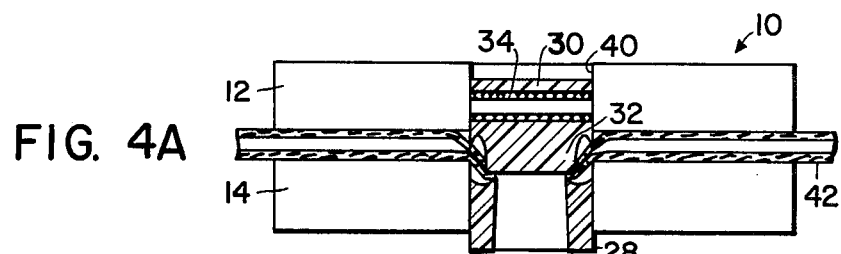
FIGS. 4A and 4B show the operation of re-opening up the vascular duct after having been closed by the operation shown in FIG. 3C by actuating the guillotine type plunger to move further downwardly from an initial position of movement (FIG. 4A) to a final position of movement (FIG. 4B) which permits the aperture located in the upper portion of the guillotine type plunger assembly to line up with the opening in both separated portions of the vascular duct or vesssel, thereby restoring an open conduit from one separated vascular duct to the other.
Figure 4B:
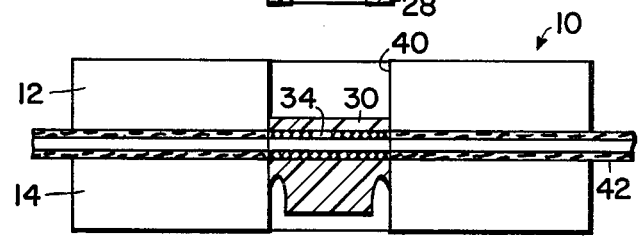
Figure 6:
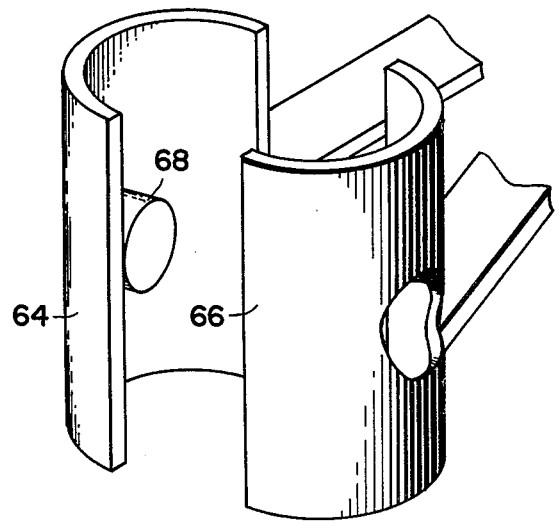
FIG. 6 is an enlarged view of the head of the clamping portions of a clamp mechanism used to insert the guillotine type plunger mechanism deeper into the vascular connector in order to restore the operation and function of the vascular duct as shown in FIGS. 4A and 4B.

Referring to FIG. 4A and 4B these figures demonstrate how the guillotine apparatus 26 of the vascular connector 10 can be again actuated, if desired, in order to permit the closed vascular duct 42 to be re-opened to permit the passage of fluid through the vascular duct 42. FIG. 4A shows the piston type member 30 being lowered further into the opening 40 which is done by means of clamp members 64 and 66 (see FIG. 6) located on a similar type of clamp mechanism (the rest of which is not shown). The clamp member 64 is positioned over the upper part 12 of the vascular connector 10 and the clamp member 66 is positioned below the lower part 14 of the vascular connector 10. Thus, plunger member 68 connected to the inside arcuate surface of the clamp member 64 is positioned above the opening 40 of the vascular connector 10 and serves to move the piston type member 30 downwardly (as shown in FIG. 4A) to its lower most portion (as shown in FIG. 4B which is determined by the depth of the plunger member 68). Thus, this action causes the severing of the duct ends and allows the fibrous member 34 (with its open conduit) located within the piston type member 30 to line up with the vascular duct 42 to now again permit the passage of fluid through the vascular duct 42. In this process of moving the guillotine type assembly downwardly, the short tubular portion 28 falls out of the vascular connector 10, along with the severed ends of the duct or vessel 42.

The vascular connector 10 and the short tubular portion 28 are made of materials which are compatible with the body and have been used previously to establish that the body will not reject the material or materials that are used.

While the invention has been particularly described and shown in reference to the preferred embodiments thereof it will be understood by those skilled in the art that various changes in form and detail and omissions may be made therein without departing from the spirit and scope of the invention.

While the illustrative example described herein of the specific use of the vascular connector 10 is for Vasectomy type uses, the vascular connector 10 can be used in other parts of the body (male or female) and for application with other ducts or vessels. Similarly, the vascular connector 10 described herein can be used in animals, if desired.

What is claimed is:

1. A method for effecting vascular duct closures comprising the steps of:
   closing a vascular connector around a portion of a vascular duct, and actuating a guillotine type plunger assembly within the vascular connector to both cut off a portion of the portion of a vascular duct and block off and hold connected the severed ends of the vascular duct portion, wherein said guillotine type plunger assembly comprising a piston type member having an extension member connected to one end of said piston type member, said piston type member having an opening extending therethrough in the same direction as said channel means, a hollow fibrous member located in said opening, and a hollow short tubular portion.

2. A method for effecting vascular duct closure and subsequent re-opening of said vascular duct comprising the steps of:
   closing a vascular connector around a portion of a vascular duct;
   actuating a guillotine type plunger assembly to one position within said vascular connector to both cut off a portion of said portion of a vascular duct and block off the severed ends of said vascular duct portion; and
   subsequently actuating said guillotine type plunger assembly to another position within said vascular connector to re-open the previously severed and blocked off ends of said vascular duct portion.

3. A method in accordance with claim 2 wherein said guillotine type plunger assembly comprising a piston type member having an extension member connected to one end of said piston type member, said piston type member having an opening extending therethrough in the same direction as said channel means, a hollow fibrous member located in said opening, and a hollow short tubular portion.

4. A method in accordance with claim 3 wherein said extension member blocking said vascular duct in said one position of said guillotine type plunger assembly.

5. A method in accordance with claim 4 wherein said opening in said piston type member communicating with said previously severed ends of said vascular duct portion in said another position of said guillotine type plunger assembly.

6. A vascular connector for effecting vascular duct closure and permitting vascular re-opening comprising, in combination, an upper portion and a lower portion, channel means located in at least one of said upper and lower portions for holding a portion of a vascular duct, and guillotine type assembly means movably mounted across said channel means for both removing a portion of said portion of the vascular duct and blocking off said channel means in one position thereof and for unblocking said channel means in another position thereof, wherein said guillotine type assembly means comprising a piston type member having an extension member connected to one end of said piston type member, said piston type member having an opening extending therethrough in the same direction as said channel means, a hollow fibrous member located in said opening, and a hollow short tubular portion.

7. A vascular connector in accordance with claim 6, including fastening means for connecting the non-pivoting ends of said upper and lower portions, said fastening means comprising a male connector portion connected to one of said upper and lower portions and a female connector portion connected to the other of said upper and lower portions, including prong means located in said channel means for gripping and holding said portion of said vascular duct.

8. A vascular connector in accordance with claim 6 wherein said piston type member and said extension member being located in one of said upper and lower portions, said hollow short tubular portion being located in the other of said upper and lower portions.

9. A vascular connector in accordance with claim 8 wherein said hollow short tubular portion having cutting means located at one end thereof adjacent said extension member for cooperation with said extension member in cutting off a portion of said portion of a vascular duct.

10. A vascular connector for effecting vascular duct closure and permitting vascular re-opening comprising, in combination, an upper portion and a lower portion, channel means located in at least one of said upper and lower portions for holding a portion of a vascular duct, and guillotine type assembly means movably mounted across said channel means for both removing a portion of said portion of the vascular duct and blocking off said channel means in one position thereof and for unblocking said channel means in another position thereof, including an opening extending transversely across and through both said upper portion and said lower portion, said guillotine type assembly means movably mounted within said opening, wherein said guillotine type assembly means comprising a piston type member having an extension member connected to one end of said piston type member, said piston type member having an opening extending therethrough in the same direction as said channel means, a hollow fibrous member located in said opening, and a hollow short tubular portion, including fastening means for connecting the non-pivoting ends of said upper and lower portions, said fastening means comprising a male connector portion connected to one of said upper and lower portions and a female connector portion connected to the other of said upper and lower portions, and including prong means located in said channel means for gripping and holding said portion of said vascular duct.

11. A vascular connector in accordance with claim 8 wherein said hollow short tubular portion having an outer diameter being substantially equal to the outer diameter of said piston type member.

12. A vascular connector in accordance with claim 11 wherein said cutting means being circular, said hollow short tubular portion having cutting means located at one end thereof adjacent said extension member for cooperation with said extension member in cutting off a portion of said portion of a vascular duct, the outer diameter of said extension member being greater than the diameter of said cutting means.

* * * * *